United States Patent [19]

Fuchs et al.

[11] 4,301,073
[45] Nov. 17, 1981

[54] PURIFICATION OF CAPROLACTAM

[75] Inventors: Hugo Fuchs; Otto-Alfred Grosskinsky; Elmar Frömmer, all of Ludwigshafen; Klaus Kartte, Beindersheim, all of Fed. Rep. of Germany

[73] Assignee: BASF Aktiengesellschaft, Fed. Rep. of Germany

[21] Appl. No.: 160,308

[22] Filed: Jun. 17, 1980

[30] Foreign Application Priority Data

Jun. 29, 1979 [DE] Fed. Rep. of Germany ....... 2926279

[51] Int. Cl.³ ............................................ C07D 201/16
[52] U.S. Cl. ............................................... 260/239.3 A
[58] Field of Search ................................. 260/239.3 A

[56] References Cited

U.S. PATENT DOCUMENTS

| 3,264,064 | 8/1966 | Nieswandt et al. | 260/239.3 A |
| 3,755,305 | 8/1973 | Schwarz et al. | 260/239.3 A |
| 3,912,721 | 10/1975 | Mattone et al. | 260/239.3 A |
| 3,914,217 | 10/1975 | Smith | 260/239.3 A |
| 4,148,793 | 4/1979 | Danziger et al. | 260/239.3 A |
| 4,154,729 | 5/1979 | Fuchs et al. | 260/239.3 A |

FOREIGN PATENT DOCUMENTS

| 1194863 | 2/1966 | Fed. Rep. of Germany | 260/239.3 A |
| 2656182 | 2/1979 | Fed. Rep. of Germany | 260/239.3 A |
| 41-11332 | 6/1966 | Japan | 260/239.3 A |

Primary Examiner—Robert T. Bond
Attorney, Agent, or Firm—Keil & Witherspoon

[57] ABSTRACT

A process for purifying caprolactam, which has been obtained by a Beckmann rearrangement, by extracting crude caprolactam with solvents, distilling the extract in the presence of alkali, and isolating pure caprolactam, wherein, in a first stage, caprolactam is distilled from the alkaline distillation residue at a bottom temperature of 130°–160° C., and is recycled to the distillation stage, the residue thus obtained is distilled, in a second stage, at a bottom temperature of 140°–180° C., and the distillate is treated with strongly acidic agents in a third stage and is then recycled to the extraction stage.

4 Claims, No Drawings

PURIFICATION OF CAPROLACTAM

The present invention relates to a process for purifying caprolactam, which has been obtained by a Beckmann rearrangement, by extracting crude caprolactam with solvents, distilling the extract in the presence of alkali, isolating pure caprolactam and working up the alkaline residue.

The distillation of caprolactam produces substantial amounts of alkaline residues which must be disposed of. Since these residues still contain substantial amounts of caprolactam, it is advisable to recover the latter from the residue, and utilize it. However, such caprolactam contains substantial amounts of impurities which, on recycling to the distillation stage, cannot be removed. In particular, the recycled caprolactam produces an unfavorable effect on the UV absorption, which is a measure of the impurities, and on the permanganate titer of pure caprolactam. Japanese Published Pat. No. 11,332/66 discloses the treatment of the alkaline distillation residue with oleum. Because of salt formation with the alkalis contained in the residues, crusts are formed on distillation and these can cause problems. Furthermore the question as to where the caprolactam can be added to the pure caprolactam without a deterioration in quality is left open.

It is an object of the present invention to carry out the purification of caprolactam in such a way that caprolactam which is recovered from residues can be recycled to the working-up procedure without the danger of impurities accumulating.

We have found that this object is achieved by a process for purifying caprolactam, which has been obtained by a Beckmann rearrangement, by extracting crude caprolactam with solvents, distilling the extract in the presence of alkali, and isolating pure caprolactam, wherein, in a first stage, caprolactam is distilled from the alkaline distillation residue at a bottom temperature of 130°–160° C., and is recycled to the distillation stage, the residue thus obtained is distilled, in a second stage, at a bottom temperature of 140°–180° C., and the distillate is treated with strongly acidic agents in a third stage and is then recycled to the extraction stage.

The novel process has the advantage that the maximum possible amount of caprolactam is obtained from the alkaline distillation residues. Furthermore the novel process makes it possible to ensure that impurities which are difficult to remove do not accumulate in the purification stages.

The caprolactam to be purified is obtained by a Beckmann rearrangement with sulfuric acid containing sulfur trioxide. A suitable process is described, for example, in U.S. Pat. No. 3,914,217. After neutralizing the rearrangement mixture, the crude caprolactam is obtained as an oil phase, which is separated off and purified.

The crude caprolactam is first extracted with solvents. Examples of suitable solvents are aromatics, e.g. benzene and toluene; the former has proved a particularly suitable solvent. An advantageous procedure to follow is to treat the crude lactam with the solvent in counter-current, crude lactam being fed to the upper part of an extraction column and benzene to the lower part. At the top of the column, a solution of caprolactam in benzene is obtained, and at the bottom an aqueous solution containing impurities. It has proved advantageous if water is additionally introduced into the upper part of the extraction zone and a part of the aqueous solution, containing impurities, obtained at the bottom end of the extraction zone is recycled into the extraction zone, in order to obtain a very concentrated aqueous solution. As a rule, from 2 to 12, especially from 2.5 to 10, parts by weight of solvent are used per part by weight of crude caprolactam. The extraction is carried out at, for example, from 40° to 65° C., under atmospheric pressure or slightly superatmospheric pressure, for example up to 1.5 bar. A suitable process is described, for example, in German Published Application DAS No. 2,656,182 or German Pat. No. 1,194,863.

The resulting caprolactam solution, which as a rule contains from 20 to 26% by weight of caprolactam and an amount of water corresponding to the solubility of water in the solvent used, is distilled in the presence of alkali. Because it is easily obtainable industrially, sodium hydroxide is advantageously used and is as a rule added in the form of a solution of from 5 to 25% strength by weight, and in an amount of from 0.05 to 0.5% by weight of NaOH, based on caprolactam to be purified. The caprolactam solution is then separated by fractional distillation and pure lactam is taken off. The distillation is advantageously carried out in 3 stages, with water being taken off at the top of the first column, volatiles being taken off at the top of the second and third columns, pure caprolactam being taken off at the side of the third column and alkaline distillation residues being discharged from the bottom of the third column. The distillation is as a rule carried out at a bottom temperature of 120°–150° C. under a pressure of from 1 to 10 mm Hg.

According to the invention, caprolactam is then distilled from the alkaline distillation residue, in a first stage, at a bottom temperature of 130°–160° C. and advantageously under a pressure of from 1 to 10 mm Hg. The caprolactam thus obtained is recycled to the pure lactam distillation stage, i.e. into the feed of the distillation columns. The distillation residue left, which as a rule still contains from 80 to 98% by weight of caprolactam, is then advantageously heated at from 140° to 180° C. under pressure of from 1 to 10 mm Hg in a distillation flask, whilst stirring, and is distilled. The alkaline residue which then remains and which contains less than 8% by weight of caprolactam, is dumped. The distillate obtained is treated, in a third stage, with strongly acidic agents.

Preferred acidic agents are sulfuric acid, phosphoric acid and strongly acid ion exchangers.

An advantageous method of carrying out the treatment is to add from 0.1 to 1% by weight of concentrated sulfuric acid or phosphoric acid to the fused caprolactam and then distil off caprolactam at 120°–180° C. under a pressure of from 1 to 10 mm Hg. In an alternative method which has proved successful, the caprolactam melt is passed over a strongly acid ion exchanger, for example a sulfonated polystyrene, advantageously at from 70° to 90° C. The residence time of the caprolactam melt over the ion exchanger is as a rule from 10 to 90 minutes.

It is an essential feature of the invention that after having been treated with the acidic agent, the caprolactam is not recycled to the distillation but to the extraction stage, i.e. into the feed line of the extraction stage.

This method makes it possible also to operate the Beckmann rearrangement at a lower temperature, advantageously from 80° to 130° C., though at lower temperatures the Beckmann rearrangement produces more impurities, whilst on the other hand the yield of caprolactam from the Beckmann rearrangement increases with decreasing temperature. Overall, it is thus possible easily to get rid of the impurities which are difficult to remove, recycle the caprolactam from the residues to the purification stages and, in addition, operate the Beckmann rearrangement under conditions which overall give a higher yield of caprolactam.

Caprolactam is used for the preparation of polycaprolactam.

The Examples which follow illustrate the invention.

EXAMPLE 1

5,386 kg/h of cyclohexanone-oxime, containing 4.2% by weight of water, are subjected to rearrangement, in a mixing loop, in the presence of 5,625 kg/h of oleum, containing 32% by weight of free sulfur trioxide, at a mean reaction temperature of 118° C. The resulting crude caprolactam, which is bonded to sulfuric acid, is liberated by neutralizing with 2,092 kg/h of gaseous ammonia in the presence of an almost saturated aqueous ammonium sulfate solution, and is separated from the ammonium sulfate solution. The 70% strength by weight aqueous crude caprolactam solution is extracted with 16,340 kg/h of benzene at 58° C. in a perforated tray column, and after distilling off the solvent 5,300 kg/h of extract caprolactam are obtained in the form of a 95% strength by weight aqueous solution. After adding 12 kg/h of 25% strength by weight sodium hydroxide solution, the water is distilled off under a pressure of 40 mm Hg. Thereafter, the system is operated under a pressure of 3 mm Hg, 200 kg/h of first runnings are taken off at the column top, 600 kg/h of a heavy fraction at the bottom of the column, and 5,000 kg/h of pure caprolactam at the side of the column.

400 kg/h are distilled from the discharged heavy fraction in a packed column at a bottom temperature of 142° C. and a pressure of 3 mm Hg, and are recycled to the main distillation stage. At the bottom of the heavy fraction distillation column, 200 kg/h of residue are discharged and fed to a thin film evaporator. At a bottom temperature of 168° C., 175 kg/h of top product are taken off under 5 mm Hg and collected in a receiver. The material discharged from the bottom of the thin film evaporator contains 1.5 kg/h of caprolactam, 20.5 kg/h of high-boiling material and 3 kg/h of alkali and is discarded.

The top product is run into a stirred kettle, with the addition of 0.35 kg/h of 96% strength by weight sulfuric acid, and is distilled from the kettle under 3–5 mm Hg, with the liquid at 136° C. After 180 hours, the feed to the kettle is discontinued and the distillation is taken to completion. The distillate has a UV number of 25–30, whilst that of the feed is about 150. The distillate (174 kg/h), which has thus been depleted in UV absorbing impurities, is recycled to the extraction stage. The residue (240.5 kg) contains 60.5 kg of $H_2SO_4$ and 180 kg of caprolactam, as well as impurities. It is neutralized with sodium hydroxide solution and then discarded. The pure lactam thus obtained has a UV number of 3.5–4.0. If, however, this intermediate acid distillation is dispensed with, the pure lactam obtained has a UV number of 5–6.

EXAMPLE 2

The procedure described in Example 1 is followed, but the distillate from the 2nd stage is not distilled over sulfuric acid but is allowed to run, at 85° C., over a strongly acid ion exchanger of the ®Amberlyst 15 type (crosslinked sulfonated polystyrene). Whilst the starting material has a UV number of 150, the lactam treated over the ion exchanger has a UV number of 70.

The UV number is determined as follows:

Principle: the absorption of the caprolactam in the spectral region from 360 to 270 nm is measured and is expressed as a characteristic number.

Analysis apparatus: 1 recording spectrophotometer (Carl Zeiss DMR/10), 1 80 ml Erlenmeyer vessel, 2 quartz cells, 1.0 cm long, with covers (i.e. presenting a 1.0 cm thick layer of the material to the beam).

Procedure: 30 g of caprolactam are dissolved in 30 g of doubly distilled water in an Erlenmeyer vessel and the solution is cooled to room temperature. It is then filled into a cell up to the calibration mark. The second cell is filled with the same doubly distilled water as is used to prepare the solution, and constitutes the comparative solution.

The covers are then placed on both cells, the ground faces are cleaned with tissue paper, and the cells are introduced into the cell holder. The spectrum is then recorded at from 370 nm to 260 nm, in accordance with the apparatus instructions. The recording speed is 120 mm/minute. The extinction is measured in range 1.

When the recording has been completed, a mark is made on the paper at intervals of 10 mm from 270 to 360 nm.

Evaluation: the extinctions at 270, 280, 290, 300, 310, 320, 330, 340, 350 and 360 nm are read off the diagram and added.

The sum of the 10 extinction values is multiplied by 2, and gives the UV number. The latter thus always relates to 100% strength caprolactam, and to a 10 cm thick layer.

We claim:

1. In a process for purifying caprolactam which has been obtained by a Beckmann rearrangement wherein the crude caprolactam obtained in the rearrangement is extracted with solvents, the solvents are distilled in the presence of an alkali and pure caprolactam is isolated, the improvement which comprises: treating the distillation residue by distilling off caprolactam from the alkaline residue in a first stage at a bottom temperature of 130°–160° C. and recycling the caprolactam obtained to the distillation stage, distilling the residue thus obtained in a second stage at a bottom temperature of 140°–180° C., treating the distillate with strongly acidic agents in a third stage, and recycling the treated distillate to the extraction stage.

2. The process of claim 1, wherein, in the third stage, caprolactam is treated with from 0.1 to 1% by weight of sulfuric acid or phosphoric acid and caprolactam is distilled off.

3. The process of claim 1, wherein, in the third stage, caprolactam melt is passed over a strongly acid ion exchanger.

4. The process of claim 1, wherein the caprolactam starting material has been obtained by a Beckmann rearrangement at from 80° to 130° C.

* * * * *